United States Patent
Tsubota et al.

(10) Patent No.: US 9,877,975 B2
(45) Date of Patent: Jan. 30, 2018

(54) AGENT FOR TREATING MEIBOMIAN GLAND DYSFUNCTION

(71) Applicant: KEIO UNIVERSITY, Tokyo (JP)

(72) Inventors: Kazuo Tsubota, Tokyo (JP); Reiko Arita, Tokyo (JP); Masataka Ito, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 14/901,518

(22) PCT Filed: Jun. 27, 2014

(86) PCT No.: PCT/JP2014/067099
§ 371 (c)(1),
(2) Date: Apr. 8, 2016

(87) PCT Pub. No.: WO2014/208709
PCT Pub. Date: Dec. 31, 2014

(65) Prior Publication Data
US 2016/0220588 A1    Aug. 4, 2016

(30) Foreign Application Priority Data

Jun. 28, 2013 (JP) .................... 2013-137020

(51) Int. Cl.
*A61K 31/593* (2006.01)
*A61K 9/06* (2006.01)
*A61K 9/00* (2006.01)

(52) U.S. Cl.
CPC .......... *A61K 31/593* (2013.01); *A61K 9/0048* (2013.01); *A61K 9/06* (2013.01)

(58) Field of Classification Search
USPC ....................... 514/20.8, 167, 168
See application file for complete search history.

(56) References Cited

U.S. PATENT DOCUMENTS

| | | |
|---|---|---|
| 6,248,732 B1 | 6/2001 | Itoh et al. |
| 2008/0312194 A1 | 12/2008 | Ousler, III et al. |
| 2013/0065867 A1* | 3/2013 | Smith ............... C07C 69/587 514/167 |
| 2014/0024625 A1 | 1/2014 | Smith et al. |

FOREIGN PATENT DOCUMENTS

| | | |
|---|---|---|
| DE | 102010026696 A1 | 1/2012 |
| EP | 0862916 A1 | 9/1998 |
| EP | 0998931 A1 | 5/2000 |
| JP | 2013-087067 A | 5/2013 |
| WO | WO 2006/004577 A2 | 1/2006 |
| WO | WO 2014/158356 A1 | 10/2014 |

OTHER PUBLICATIONS

Sullivan et al., *Advances in Experimental Medicine and Biology*, 506(Pt. A): 441-447 (2002).
Japanese Patent Office, International Search Report in International Patent Application No. PCT/JP2014/067099 (dated Sep. 16, 2014).
European Patent Office, Supplementary European Search Report in European Patent Application No. 14818800 (dated Jun. 8, 2016).
Hefti, "What Are Nutritional Supplements? Information You Must Know!," Supplements-And-Health.com, pp. 1-2 (downloaded from http://www.supplements-and-health.com/nutritional-supplements-information.html on May 15, 2017).

* cited by examiner

*Primary Examiner* — Pancham Bakshi
(74) *Attorney, Agent, or Firm* — Leydig, Voit & Mayer, Ltd.

(57) ABSTRACT

The present invention aims to provide an agent for treating meibomian gland dysfunction. The present invention provides an agent for treating meibomian gland dysfunction, which contains activated vitamin $D_3$ or a derivative thereof as an active ingredient.

8 Claims, 1 Drawing Sheet

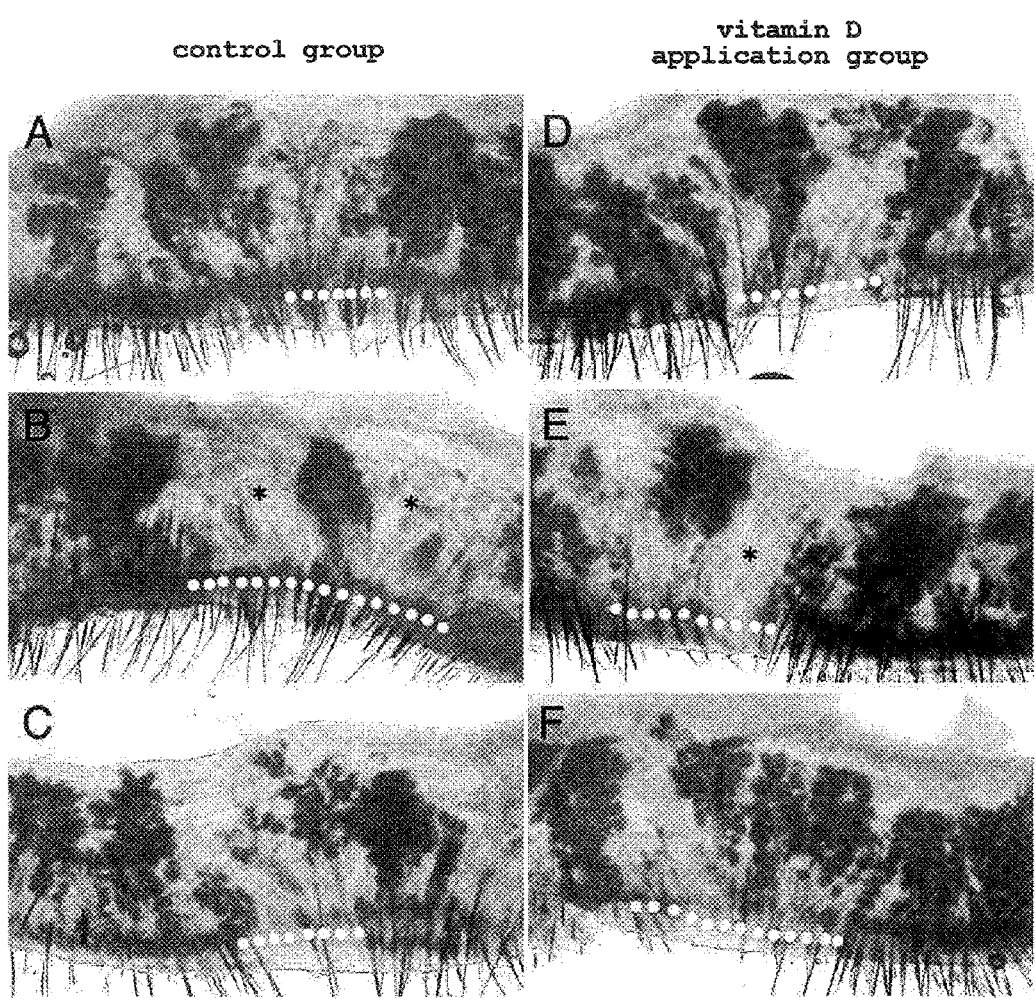

AGENT FOR TREATING MEIBOMIAN GLAND DYSFUNCTION

CROSS-REFERENCE TO RELATED APPLICATIONS

This patent application is the U.S. national phase of International Patent Application No. PCT/JP2014/067099, filed Jun. 27, 2014, which claims the benefit of Japanese Patent Application No. 2013-137020, filed on Jun. 28, 2013, which are incorporated by reference in their entireties herein.

TECHNICAL FIELD

The present invention relates to an agent for treating meibomian gland dysfunction. Particularly the present invention relates to an agent for treating meibomian gland dysfunction containing activated vitamin $D_3$ as an active ingredient. The present invention further relates to a method of treating meibomian gland dysfunction. Particularly, the present invention relates to a method of treating meibomian gland dysfunction, comprising administering an effective amount of a pharmaceutical composition containing an activated vitamin $D_3$ as an active ingredient.

BACKGROUND ART

Meibomian gland is a sebaceous gland present in the tarsal plate and has orifices around the top and bottom eyelid margins. The lipid (meibum) secreted from the meibomian gland is distributed on the eyelid margin and the outermost layer of the lacrimal fluid, and acts to suppress evaporation of lacrimal fluid, promote the stability of lacrimal fluid, promote the extension of lacrimal fluid on the eye surface, suppress outflow of lacrimal fluid from the eyelid margin onto the skin, and the like (non-patent document 1).

While meibomian gland dysfunction (MGD) is clinically used to refer to an abnormal state of meibomian gland function (non-patent document 2), it has not attracted attention clinically in general ophthalmology for the reasons that (1) inflammation and resident bacterium may or may not be involved and clinical images vary, (2) the severity varies widely from a mild case to a severe case, (3) definition and diagnostic standard have not been established heretofore, (4) only a few treatments are effective, and the like.

In fact, however, a considerable proportion of the patients who visited ophthalmological clinic with symptoms such as ocular discomfort and the like as the chief complaints was caused by MGD, and many patients are considered to have been suffering from reduced QOL. Although MGD is a clinically important disease, the study thereof has not been conducted much for the above-mentioned reasons and, as the situation stands, an effective therapeutic agent has not been found as yet.

On the other hand, while an ophthalmic composition containing activated vitamin D (patent document 1), an external preparation containing vitamin Ds, vitamin Ks (patent document 2), a therapeutic agent for dry eye, which contains activated vitamin $D_3$ (patent document 3) and the like have been reported, none of them describe or suggest that activated vitamin $D_3$ has a therapeutic or improving effect on meibomian gland dysfunction.

DOCUMENT LIST

Patent Documents patent document 1: WO 96/29079
patent document 2: JP-B-3738450
patent document 3: JP-A-10-316574

Non-Patent Documents non-patent document 1: Foulks G N, Bron A J: Ocul Surf 1: 107-126, 2003.
non-patent document 2: Gutgesell V J, Stern G A, Hood C I: Am J Ophthalmol 94: 383-387, 1982.
non-patent document 3: Shiro Amano et al., Journal of the eye; 27(5); 627-631 (2010)

SUMMARY OF THE INVENTION

Problems to be Solved by the Invention

An object of the present invention is to provide an agent for treating meibomian gland dysfunction. The present invention also aims to provide an agent for treating meibomian gland dysfunction accompanying an inflammatory diseases, lipid overaccumulation in duct, or a decrease in the meibum secretion.

Means of Solving the Problems

In view of the above-mentioned problems, the present inventors have found that activated vitamin $D_3$ is effective for meibomian gland dysfunction, and completed the present invention.

Accordingly, the present invention provides the following.
(1) An agent for treating meibomian gland dysfunction, which comprises an activated vitamin $D_3$ or a derivative thereof as an active ingredient.
(2) The agent of the above-mentioned (1), which is an external preparation.
(3) The agent of the above-mentioned (2), which is in a dosage form of ointment.
(4) The agent of any of the above-mentioned (1)-(3), wherein the activated vitamin $D_3$ or a derivative thereof is at least one kind selected from Tacalcitol, Calcipotriol, and Maxacalcitol.
(5) The agent of any of the above-mentioned (1)-(4), wherein the meibomian gland dysfunction accompanies an inflammatory disease.
(6) The agent of the above-mentioned (5), wherein the inflammatory disease is one kind selected from meibomian gland inflammation, superficial (punctate) keratitis, and blepharitis.
(7) The agent of any of the above-mentioned (1)-(4), wherein the meibomian gland dysfunction accompanies lipid overaccumulation in duct.
(8) The agent of any of the above-mentioned (1)-(4), wherein the meibomian gland dysfunction accompanies a decrease in meibum secretion.
(9) The agent of any of the above-mentioned (1)-(4), wherein the meibomian gland dysfunction accompanies an ocular discomfort, a foreign sensation, and/or an oppressive feeling.
(10) A method of treating meibomian gland dysfunction, comprising administering an effective amount of an activated vitamin $D_3$ or a derivative thereof to a target in need thereof.

(11) An activated vitamin $D_3$ or a derivative thereof for use for the treatment of meibomian gland dysfunction.
(12) The agent of any of the above-mentioned (1)-(4), wherein the meibomian gland dysfunction accompanies atrophy of the meibomian gland.
(13) A method for the prophylaxis or treatment of meibomian gland atrophy in a mammal, comprising administering an effective amount of an activated vitamin $D_3$ or a derivative thereof to the mammal.
(14) A method of suppressing meibomian gland atrophy in a mammal, comprising administering an effective amount of an activated vitamin $D_3$ or a derivative thereof to the mammal.

Effect of the Invention

The present invention using an activated vitamin $D_3$ as an active ingredient suppresses atrophy of the meibomian gland. Accordingly, the present invention is useful as an agent for treating meibomian gland dysfunction.

BRIEF DESCRIPTION OF THE DRAWINGS

FIG. 1 shows suppression of atrophy of the meibomian gland in a meibomian gland atrophy model by the therapeutic agent of the present invention. The atrophy of the meibomian gland was produced by cauterization of an orifice (diathermy cauterization). A-C show case groups applied with petrolatum after diathermy cauterization, D-F show case groups applied with activated vitamin $D_3$ ointment (Oxarol ointment) after diathermy cauterization. A-C show stereomicroscopic images of upper eyelid collected after 10-day cessation of the drug after application of petrolatum for 6 consecutive days (once per day) from 2 days after cauterization, and D-F show those of upper eyelid collected after 10-day cessation of the drug after application of Oxarol ointment for 6 consecutive days (once per day) from 2 days after cauterization. All the lower photographs show those on the optic fissure side, and all the upper photographs show those on the vertex side.

DESCRIPTION OF EMBODIMENTS

The present invention is explained in the following. Unless particularly indicated, the terms used in the present specification have the meanings generally used in the pertinent field.

Meibomian gland dysfunction (MGD) is a diffuse or localized abnormality in the functions of the meibomian gland due to various causes and, in many cases, it accompanies a chronic ocular discomfort. MGD is largely divided into a hypo-secretory type and a hyper-secretory type, and the clinical frequency is higher in the secretion decrease type. The secretion decrease type MGD includes a primary type such as obstructive, atrophicus, congenital types and the like, and a type that occurs following atopy, Stevens-Johnson syndrome, graft-versus-host disease, trachom and the like. In a hypo-secretory type of MGD, obstructive ones in the primary MGDs show the highest frequency. In the obstructive MGD in the primary MGDs, keratinized materials are overaccumulated in the meibomian gland duct, secretion of meibum decreases, and atrophy of the acinus of the meibomian gland gradually progresses. Atrophicus MGD in the primary MGDs does not occur following obstruction of the duct, but refers to one wherein acinus is primarily atrophied. In the secondary MGDs, obstruction of the orifice of the meibomian gland occurs due to various causes, and secretion of the meibum decreases.

The diagnostic criteria of the hypo-secretory type of meibomian gland dysfunction include subjective symptoms, abnormal finding in the periphery of the meibomian gland orifice and positive finding of obstruction of the orifices of the meibomian gland (non-patent document 3).

Examples of the subjective symptom include an ocular discomfort (rumbling feeling, bleary feeling etc.), a foreign sensation, an oppressive feeling and the like.

Examples of the abnormal finding in the periphery of the opening part of meibomian gland include vasodilation, anterior or posterior transfer of mucocutaneous junction, eyelid margin disarrangement and the like.

Examples of the finding of obstruction of the meibomian gland orifice include findings called plugging, putting, ridge; decreased pulsion of fats and oils from the meibomian gland; and the like.

Furthermore, when MGD accompanies an inflammatory disease, or lipid overaccumulation in duct, a decrease in the meibum secretion is also accompanied sometimes, and such MGD is also a preferable target to which the present invention is applied. Examples of the inflammatory diseases include meibomian gland inflammation, superficial (punctate) keratitis, blepharitis and the like.

Examples of the laboratory finding to be referenced for the hypo-secretory type meibomian gland dysfunction other than these include meibography. Meibography is an apparatus for direct morphological observation of the meibomian gland by permeating light from the backside of reversed eyelid, or observing the eyelid with an infrared camera or infrared filter. In the observation by meibography, defluxion or atrophy of the meibomian gland is observed in a hypo-secretory type meibomian gland dysfunction. In the observation with a confocal microscope, a decrease in the density of the meibomian acinus is observed in a thypo-secretory type MGD and the like (non-patent document 3).

In the present specification, atrophy of the meibomian gland refers to a state where the volume of an organ or tissue that grew to the normal volume has decreased due to various reasons. The "atrophy of the meibomian gland" described in the present specification can include total or partial atrophy of the meibomian gland. In the present specification, atrophy of the meibomian gland can include, but is not limited to, atrophy of any of the parts constituting the meibomian gland such as secretory acinus, ductule, central duct, excretory duct and the like, or a combination thereof. The atrophy of the meibomian gland can include meibomian gland having a volume that decreased to not more than about 99.99%, not more than about 99.9%, not more than about 99%, not more than about 95%, not more than 90%, not more than 80%, not more than 70%, not more than 60%, not more than 50%, not more than 40%, not more than 30%, not more than 20%, not more than 10% or not more than 1%, relative to the volume of the normal meibomian gland. Examples of the atrophy of the meibomian gland that accompanies a decrease in the volume of the meibomian gland include, but are not limited to, atrophy due to the defluxion of glandular tissue, lack of acinus, a decrease in the cell number and the like. In a preferable embodiment of the present invention, the meibomian gland dysfunction accompanies atrophy of the meibomian gland.

Examples of the activated vitamin $D_3$ contained as an active ingredient in the present invention include Calcitriol (1,25-dihydroxyvitamin $D_3$), Tacalcitol (1α,24(R)-dihydroxyvitamin $D_3$) and the like. The activated vitamin $D_3$ derivative may be any as long as it is a compound showing an activated vitamin D₃-like activity and examples thereof include Calcipotriol (1α,24(OH)₂-22-en-24-cyclopropyl-vitamin D₃), Alfacalcidol, Falecalcitriol (1,25-dihydroxy-26,27-hexafluoro-vitamin D₃), Maxacalcitol (22-oxa-1α,25-dihydroxyvitamin D₃) and the like. Of these, Tacacitol, Calcipotriol and Maxacalcitol are preferable, and Maxacalcitol is more preferable. Commercially available products can be used as these. For example, in the case of Tacalcitol, "Bonalfa (registered trade mark) High ointment" and "Bonalfa (registered trade mark) High loation" are commercially available; in the case of Calcipotriol, "Dovonex (registered trade mark) ointment" is commercially available, and in the case of Maxacalcitol, "Oxarol (registered trade mark) ointment" and "Oxarol (registered trade mark) lotion" are commercially available. The activated vitamin D₃ may be used alone, or plural kinds thereof may be used in combination.

The agent for treating meibomian gland dysfunction of the present invention, which contains an activated vitamin D₃ or activated vitamin D₃ derivative (hereinafter sometimes to be generically referred to as activated vitamin D₃s) as an active ingredient (hereinafter to be also generically referred to as the treatment agent of the present invention) can be administered by any route, and a preferable administration route is topical administration (e.g., ointment, eye drop, liquid medicine, lotion, cream). The mode of administration of the treatment agent of the present invention can be appropriately determined depending on whether the application to meibomian gland dysfunction is for a prophylactic object or treatment object, severity of the symptom and the like. A preferable dosage form is an external preparation, which is more preferably an ointment (eye ointment), eye drop and liquid medicine, and a particularly preferable dosage form is an ointment.

The treatment agent of the present invention can be formed according to the administration form by a conventional method by adding other components to the activated vitamin D₃s. For example, when it is formed as an ointment, petrolatum, higher alcohol, beeswax, vegetable oil, polyethylene glycol and the like are added. When it is formed as a cream, for example, an oil phase added with fats and oils, wax, higher fatty acid, higher alcohol and the like is emulsified by a surfactant, and the emulsion is formed as an emulsion cream. When it is formed as a lotion, ethanol, glycerol, propylene glycol and the like may be added or emulsion lotion comprising an oil phase, an aqueous phase, and a surfactant is formed.

When a preparation containing various activated vitamin D₃s as an active ingredient is commercially available, such may be used, since it is convenient and preferable.

In the present specification, the term "treatment" encompasses any management of the diseases including prophylaxis, treatment, improvement, and prevention of exacerbation.

The activated vitamin D₃ or activated vitamin D₃ derivative of the present invention, and the treatment agent of the present invention containing same are preferably administered immediately after an administration subject such as mammal, particularly human, is diagnosed to have a risk of meibomian gland dysfunction and before the onset thereof (prophylactic treatment). Alternatively, it is administered immediately after the administration subject is diagnosed to have developed meibomian gland dysfunction (therapeutic treatment). The treatment plan can be appropriately determined according to the kind of the activated vitamin D₃s to be used, dose, administration route, cause, and symptoms.

The administration subject of the treatment agent of the present invention is an animal having the meibomian gland, preferably mammal.

While the content of the activated vitamin D₃s in the treatment agent of the present invention varies depending on the kind of the activated vitamin D₃s to be used, it is generally about 0.0001-about 0.1 wt %, preferably about 0.001-about 0.01 wt %, relative to the whole preparation. To be specific, the content is, for example, about 0.001-about 0.004 wt % for Tacalcitol, about 0.0025-about 0.01 wt % for Calcipotriol, about 0.00125-about 0.005 wt % for Maxacalcitol. When two or more kinds of activated vitamin D₃s are used in combination, the contents are preferably increased or decreased as appropriate according to the efficacy of each.

While the dose of the activated vitamin D₃s in the present invention can be appropriately determined according to the kind of the activated vitamin D₃s to be used, age and body weight of the administration target, symptom, dosage form, administration method and the like, it is generally determined within the range clinically used. When activated vitamin D₃s is commercially available as a preparation, the dose of the activated vitamin D₃s can be set according to the package insert thereof.

In one embodiment wherein it is formed as an external preparation for topical administration, the amount of the active ingredient is about 10-about 200 μg for Tacalcitol, about 25-about 500 μg for Calcipotriol, and about 12.5-about 250 μg for Maxacalcitol. When two or more kinds of activated vitamin D₃s are used in combination, the contents are preferably increased or decreased as appropriate according to the efficacy of each. The external preparation is administered (e.g., applied) to the upper eyelid one to several times per day.

Also, administration in a sustained manner is possible depending on the symptom or disease state, and a long-term treatment may be required.

The treatment agent of the present invention may contain other pharmaceutically active compound as long as it does not inhibit the effect of the invention.

The treatment agent of the present invention permits simultaneous administration of the treatment agent and other medicament as long as it does not inhibit the effect of the invention. The "simultaneous administration" means administration of other medicament by the same or different administration route before, simultaneously with (e.g., in the same preparation or different preparation) or after administration of the composition of the present invention. Examples of other medicament include anti-infection agent, anti-inflammatory agent, nerve agent, hormone agent and the like.

Examples of the anti-inflammatory agent include steroids (e.g., hydrocortisone, prednisolone, dexamethasone, fluorometholone) and non-steroidal anti-inflammatory agents (e.g., ketorolac tromethamine, indomethacin, flurbiprofen sodium, nepafenac, bromfenac, suprofen, diclofenac).

Examples of the antiinfection agent include mupirocin, antianaerobic anti-infection agent (e.g., chloramphenicol, clindamycin), antifungal antibiotic anti-infection agent (e.g., amphotericin b, clotrimazole, fluconazole, ketoconazole), macrolide antibiotic antiinfection agent (e.g., azithromycin, erythromycin), β-lactam antibiotic anti-infection agent (e.g., aztreonam, imipenem), penicillin antibiotic anti-infection agent (e.g., nafcillin, oxacillin, penicillin G, penicillin V), quinoline antibiotic anti-infection agent (e.g., ciprofloxacin, norfloxacin), tetracycline antibiotic antiinfection agent (e.g., doxycycline, minocycline, tetracycline), antiprotozoal anti-infection agent (e.g., atovaquone, dapsone) and the like.

Examples of the hormone agent include amine derivative hormone which is tyrosine or tryptophan derivative of amino acid; peptide hormone such as TRH, vasopressin and the like; protein hormone such as insulin and growth hormone and the like. Examples of the hormone agent having a more complicated structure include glycoprotein hormone such as luteinizing hormone, follicle-stimulating hormone and thyroid-stimulating hormone and the like; and hormone (e.g., testosterone, cortisol, calcitriol, prostaglandin) which are derived from lipid such as linoleic acid, arachidonic acid and the like, or phospholipid.

Examples of the nerve agent include neurotransmitters (e.g., acetylcholine, ATP, glycine, glutamic acid, dopamine, norepinephrine, epinephrine, octopamine, serotonin (5-hydroxytryptamine), β-alanine, histamine, γ-aminobutyric acid (GABA), taurine, aspartic acid, nitric oxide) and neuropeptide (e.g., hypothalamus hormone such as oxytocin and vasopressin and the like; hypothalamus releasing or inhibiting hormone such as corticotropin-releasing hormone, growth hormone-releasing hormone (GHRH), luteinizing hormone-releasing hormone (LHRH), somatostatin growth hormone release-inhibiting hormone and thyrotropin-releasing hormone (TRH) and the like; tachykinins such as neurokinin a (substance K), neurokinin b, neuropeptide K and substance P and the like; opioid peptides such as b-endorphin, dynorphin and methionine- and leucine-enkephalin and the like; NPY and related peptide thereof such as neuropeptide tyrosine (NPY), pancreas polypeptide and peptidetyrosine-tyrosine (PYY) and the like; VIP-glucagon family member such as glucagon-like peptide-1 (GLP-1), peptide histidine isoleucine (PHI), pituitary adenylate cyclase-activating peptide (PACAP) and vasoactive intestinal polypeptide (VIP) and the like; and brain natriuretic peptide, calcitonin gene-related peptide (CGRP) (a- and b-type), cholecystokinin (CCK), galanin, pancreatic isletamyloid polypeptide (IAPP), i.e., amylin, melanin-concentrating hormone (MCH), melanocortin, neuropeptide FF (F8Fa), neurotensin, parathyroid hormone-related protein, agouti gene-related protein (AGRP), cocaine- and amphetamine-regulated transcript (CART)/peptide, endomorphine-1 and -2,5-HT-modulin, hypocretin/orexin, nociceptin/orphanin FQ, nocistatin, prolactin releasing peptide, secretoneurin and urocrtin).

Furthermore, vasoconstrictor, antiallergic agent, anesthetics, analgesic and the like can also be used in combination, and those generally used in the pertinent field can be selected as appropriate.

The contents disclosed in any publication cited in the present specification, including patents and patent applications, are hereby incorporated in their entireties by reference, to the extent that they have been disclosed herein.

While the present invention is explained in detail in the following by referring to Examples, the present invention is not limited in any way by the following Examples. In addition, the reagents and materials to be used are commercially available unless particularly limited.

EXAMPLES (Method)
a. Generation of Meibomian Gland Atrophy Mouse Model

Meibomian gland atrophy mouse models were generated by the following steps by meibomian gland orifices cauterization.

(1) 8- to 10-week-old C57BL6 mice (CLEA Japan, Inc.) were used.

(2) Under systemic anesthesia by pentobarbital intraperitoneal injection, 2-5 meibomian gland orifices near the center of the right upper eyelid were cauterized by diathermy. The energizing time was within 0.75 second per one orifice. The upper left eyelid was left unattended and used as a non-treatment control.

(3) The mice were sacrificed 1-3 weeks after the operation. The upper eyelids were collected, and the skin and conjunctival epithelium were manually removed as much as possible. The upper eyelids free of the skin and conjunctival epithelium were photographed and observed for meibomian gland silhouette under a stereoscopic microscope by using a permeation light source.

(4) The photographed meibomian gland silhouette images were treated using an Adobe Photoshop, and the area was quantified using an image analysis software ImageJ.

(5) Eight meibomian glands in total of 3 mice were cauterized by the above-mentioned method, and the meibomian gland silhouette area was quantified 3 weeks after the operation. As a result, the area of the meibomian gland after cauterization was 0.14 mm$^2$ per one meibomian gland, whereas 0.21 mm$^2$ per one meibomian gland in the left eyelid non-treatment control, thus showing a significant decrease in the area in the cauterization group (p=0.0037, t-test).

b. Oxarol Application Experiment (1) Diathermy cauterization was performed by the method of the above-mentioned a (1)-(2), and meibomian gland atrophy mice were produced. Six mice were divided into two groups, and used as an activated vitamin D group and a control group.

(2) Oxarol ointment (Maxacalcitol ointment; 25 μg/g) was applied to the activated vitamin D group and petrolatum was applied to the control group, each once per day for 6 consecutive days from two days after cauterization (experiment schedule is shown below). Oxarol or petrolatum in about half the size of a sesame granule was applied to the upper eyelid. After final application at 7 days post-operation, the mice were sacrificed at 17 days post-operation, and the upper eyelid was collected.

Experiment Schedule

| days after operation | treatment |
|---|---|
| 0 | diathermy cauterization |
| 1 | cessation of drug |
| 2 | application of Oxarol or petrolatum |
| 3 | application of Oxarol or petrolatum |
| 4 | application of Oxarol or petrolatum |
| 5 | application of Oxarol or petrolatum |
| 6 | application of Oxarol or petrolatum |
| 7 | application of Oxarol or petrolatum |
| 8-16 | cessation of drug |
| 17 | slaughter |

(Results)

The results of observation and photographing of upper eyelid meibomian gland silhouette under a stereoscopic microscope by using a permeation light source are shown in FIG. 1.

A-C show silhouette images of the upper eyelid applied with diathermy cauterization, and petrolatum for 6 consecutive days (once per day) from two days after the operation, and collected at 17 days after the operation. D-F show silhouette images of the upper eyelid similarly applied with Oxarol ointment and collected at 17 days after the operation.

All the parts that look like a dark shadow of thick trees show the meibomian gland.

Since depigmentation occurs at the part where diathermy cauterization was performed (dotted line), the margin of the eyelid looks whiter than the peripheral part. The hair root decreased in the part where diathermy cauterization was performed, and acinus near the meibomian gland orifice disappeared. These are considered to be the direct effects of the cauterization.

It was found by comparison of the silhouettes of the meibomian gland that remained in the periphery of the cauterization region that the loss region (* in Figures) is less in D-F than in A-C. The area of the silhouette of the meibomian gland was quantified by the method of the above-mentioned a (3)-(4). As a result, the area of one meibomian gland in the cauterization region was 0.12 mm$^2$ in the Oxarol application group (vitamin D application group), whereas it was 0.056 mm$^2$ in the petrolatum application group, and atrophy was significantly suppressed in the Oxarol application group (p=0.032, t-test).

Accordingly, it has been clarified that the treatment agent of the present invention has an action to improve atrophy of the meibomian gland.

INDUSTRIAL APPLICABILITY

The therapeutic agent of the present invention containing activated vitamin $D_3$ as an active ingredient can suppress atrophy of the meibomian gland. Accordingly, the present invention is useful as an agent for treating meibomian gland dysfunction.

This application is based on patent application No. 2013-137020 filed in Japan (filing date: Jun. 28, 2013), the contents of which are encompassed in full herein.

The invention claimed is:

1. A method of treating meibomian gland dysfunction, comprising administering an effective amount of an activated vitamin $D_3$ or a derivative thereof as an active ingredient in an ointment to a target in need thereof.

2. The method according to claim 1, wherein the activated vitamin $D_3$ or a derivative thereof is at least one kind selected from the group consisting of Tacalcitol, Calcipotriol, and Maxacalcitol.

3. The method according to claim 1, wherein the meibomian gland dysfunction accompanies an inflammatory disease.

4. The method according to claim 3, wherein the inflammatory disease is one kind selected from the group consisting of meibomian gland inflammation, superficial (punctate) keratitis, and blepharitis.

5. The method according to claim 1, wherein the meibomian gland dysfunction accompanies lipid overaccumulation in duct.

6. The method according to claim 1, wherein the meibomian gland dysfunction accompanies a decrease in meibum secretion.

7. The method according to claim 1, wherein the meibomian gland dysfunction accompanies an ocular discomfort, a foreign sensation, and/or an oppressive feeling.

8. The method according to claim 1, wherein the meibomian gland dysfunction accompanies atrophy of the meibomian gland.

* * * * *